United States Patent [19]

Heyman

[11] 4,308,642
[45] Jan. 5, 1982

[54] HOSPITAL UTILITY DEVICE

[76] Inventor: Arnold Heyman, 3573 Terrace View Dr., Encino, Calif. 91316

[21] Appl. No.: 152,194

[22] Filed: May 22, 1980

Related U.S. Application Data

[63] Continuation of Ser. No. 947,520, Oct. 2, 1978, abandoned.

[51] Int. Cl.³ .............................................. A44B 21/00
[52] U.S. Cl. ............... 24/306; 128/DIG. 26; 248/68 R; 24/334
[58] Field of Search ............... 248/49, 74 R, 65, 68 R; 24/81 TH, 81 SH, 81 H, 81 HH, 16 R, 73 SH; 128/DIG. 15, DIG. 26

[56] References Cited

U.S. PATENT DOCUMENTS

| | | | |
|---|---|---|---|
| 3,128,514 | 4/1964 | Parker et al. | 24/204 X |
| 3,179,991 | 4/1965 | Seal | 24/73 SH |
| 3,374,508 | 3/1968 | Slimovitz | 24/3 R |
| 3,818,905 | 6/1974 | Lebold | 128/DIG. 15 X |
| 3,834,380 | 9/1974 | Boyd | 128/133 |
| 3,857,397 | 12/1974 | Brosseau | 128/DIG. 15 X |
| 3,896,527 | 7/1975 | Miller | 24/81 HS |
| 4,074,397 | 2/1978 | Rosin | 128/DIG. 26 X |
| 4,088,136 | 5/1978 | Hasslinger | 24/16 R X |
| 4,096,863 | 6/1978 | Irving | 24/16 R X |
| 4,122,857 | 10/1978 | Haerr | 128/DIG. 26 X |

FOREIGN PATENT DOCUMENTS 624676 8/1961 Canada ....................... 128/DIG. 26

*Primary Examiner*—J. Franklin Foss
*Attorney, Agent, or Firm*—Spensley, Horn, Jubas & Lubitz

[57] ABSTRACT

A device having special utility for holding medically-related conduits in a hospital setting is disclosed. The device comprises a generally flat, flexible pad having a gripper at one end thereof. The gripper is configured so as to selectively join the pad to a bedsheet, hospital gown or the like. A tape is disposed on the pad and extends across one surface thereof. The tape is configured such that the conduits can be secured between the tape and the pad. One surface of the tape is made of a material which selectively engages the surface of the pad such that the tape may be easily removed from and secured to the pad.

11 Claims, 3 Drawing Figures

U.S. Patent   Jan. 5, 1982   4,308,642
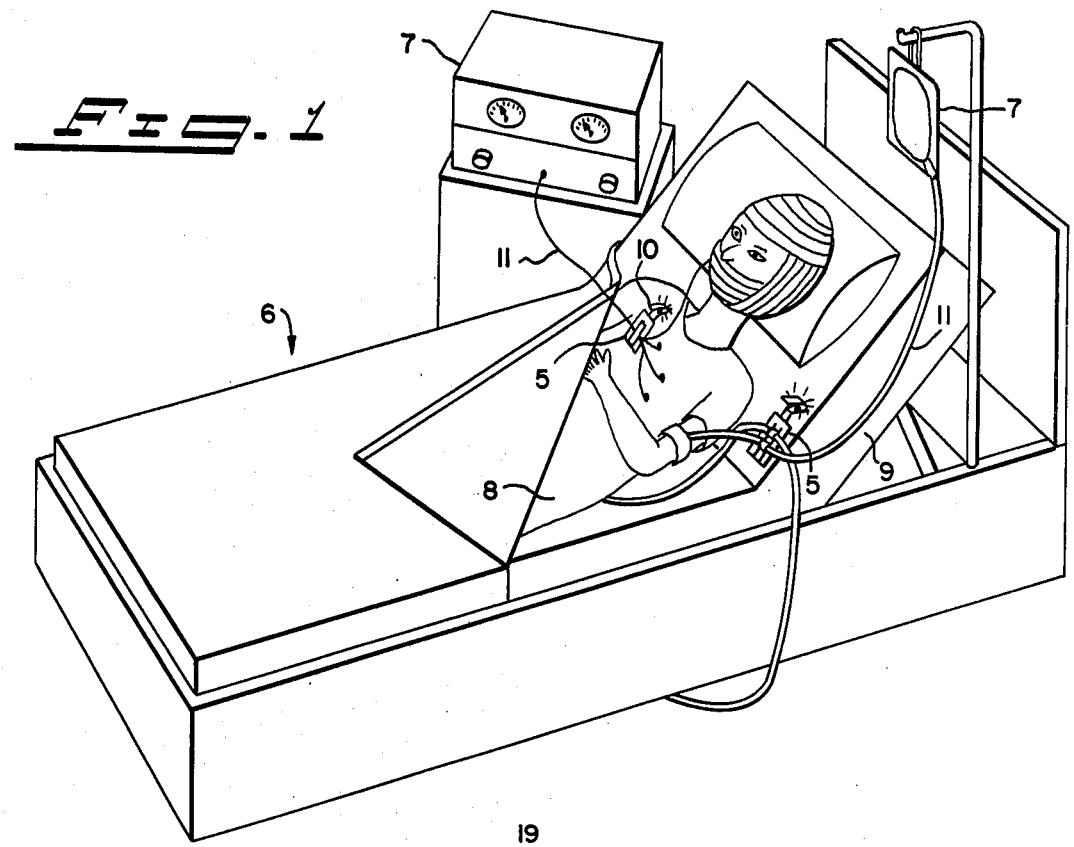
Fig. 1
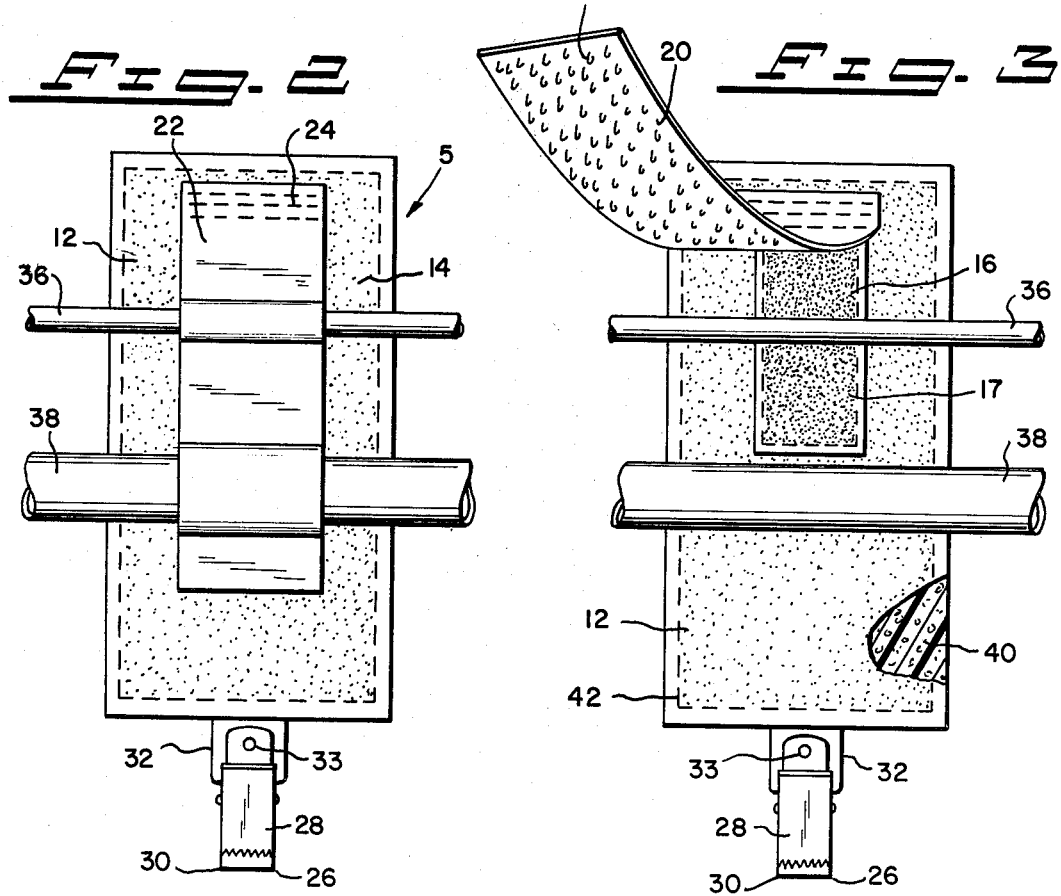
Fig. 2
Fig. 3

HOSPITAL UTILITY DEVICE

This is a continuation of application Ser. No. 947,520, filed Oct. 2, 1978 now abandoned.

BACKGROUND OF THE INVENTION

1. Field of the Invention

This invention relates to the field of hospital devices, and more particularly, to a device for holding medically-related conduits such as tubing, cords and the like in a secure manner.

2. Prior Art

The use of various medical conduits joined to the patient for a variety of purposes is well recognized in the medical arts. One example of such devices is a catheter which is joined to the patient so as to permit urine drainage to take place while the patient remains in bed. In the use of a typical catheter, after it is appropriately inserted, a long conduit joins the catheter to a drainage bag. The problem with such conduit is that if unsupported it may place undue stress and irritate in the area of the insertion and it can become entangled with the patient whereby it may either become disengaged from the patient or from the bag. To prevent this from happening and to provide support for the conduit, the conduit is usually pinned to the bedsheet by the use of a hook-like member, rubber bands and pins. The problem with such a system for joining the conduit to the bedsheet is that after a number of uses, the bedsheet, especially in certain areas, becomes ridden with holes. These holes lead to tears in the bedsheet and ultimately to the destruction of the sheet. Hospital bedsheets so destroyed add to the high costs associated with staying in a hospital. Further, the use of the hook-member arrangement is awkward and time consuming. It is also difficult to sterilize and reuse.

In other situations, it is necessary to attach electronic sensing devices to the patient or yet other tubes such as I.V. tubes and the like. To prevent movement of the tubing or electrical wires or cords to the patient, such tubing and/or cords are pinned to the bedsheets, to the surgical sheets, to the patient's bandages, or to the gown which the patient is wearing. Again, the same problem arises. The pins used to hold the tubes and cords in position cause holes in the sheets. These holes not only result in the destruction of the sheets but also result in a deterioration of sterile conditions attendant various surgical operations.

Recently, a pad has been introduced into the marketplace which contains a sticky back. This enables the pad to be attached to the sheet, gown or like material. The pad has a section which can be twisted so as to join the tubing or cord to the pad. The problems with such pads are that the means by which the tube or cord is joined to the pad, limits the number of tubes/cords which can be so joined. Further, because the pad is attached to the bed by the use of a sticky back, the pad has a very limited life and cannot be repeatedly washed. This is a significant shortcoming. Thus, while such a pad does not lead to the destruction of the material to which it is attached, it is used only once, and the number of tubes or cords attached to it is limited.

The present invention overcomes these problems associated with prior art devices by providing a pad which can be easily joined to a bedsheet or like material in a non-obtrusive manner such that the bedsheet or other material is not destroyed. Further, the device of the present invention enables a plurality of tubes and/or cords to be secured to the pad.

BRIEF SUMMARY OF THE INVENTION

A pad for holding medically related items such as electrical conduits, cords, tubing and the like is described. The pad enables such medical items to be joined to the pad in a secure fashion. The pad is flexible and has a generally flat, rectangular configuration with a grip means located at one end thereof. The grip means is configured to selectively join the pad to a selected surface in such a manner so as to achieve the necessary joining but so as not to cause punctures.

An elongated member such as a piece of tape is joined to the pad at the other end thereof. The tape has a surface containing a plurality of joining members which selectively engages a surface of a pad. The joining members permit the tape to be easily joined to and removed from the surface of the pad a number of times without destruction of either the surface of the pad or the surface of the tape.

It is therefore one object of the present invention to provide a device which can be selectively joined to a bedsheet, hospital gown, or bandage in a non-obtrusive manner.

It is yet another object of the present invention to provide a device which can be reused a number of times without adversely affecting the functioning of the device.

The novel features which are believed to be characteristic of the invention, both as to its organization and method of operation, together with further objectives and advantages thereof will be better understood from the following description considered in connection with the accompanying drawings in which a presently preferred embodiment of the invention is illustrated by way of example. It is expressly understood, however, that the drawings are for the purpose of illustration and description only, and are not intended as a definition of the limits of the invention.

BRIEF DESCRIPTION OF THE DRAWINGS

FIG. 1 is a view showing the device of the present invention in a hospital setting;

FIG. 2 is a top view of the device of the present invention; and

FIG. 3 is yet another top view of the device of the present invention.

DETAILED DESCRIPTION OF THE INVENTION

Referring first to FIG. 1, one can see the device 5 of the present invention in a typical hospital setting. In many situations, instruments 7 have to be coupled to the patient 8. Such instruments 7 may include, for example, a catheter apparatus, electronic devices such as EEG and EKG machines, and the like. In many situations, instruments 7 would be attached to the patient 8 by means of tubing or electrical cords 11. For ease of reference, tubing and cords 11 are referred to herein as conduits 11. The conduits 11 extend from the instruments 7 and are long enough to permit some movement of the patient 8. However, the conduits 11 are preferably attached to the bed 6, bedsheet 9 or hospital gown 10 to prevent unnecessary movement of the conduits 11. The specific point of attachment is governed by a number of factors including, what the conduit is for, type of patient, etc. The device 5 of the present invention enables conduits 11 to be easily joined to the bedsheet 9, hospital gown 10 or any other generally flexible surface.

Referring now to FIGS. 2 and 3, one can see that the device 5 is comprised of a generally rectangular pad 12 having a first surface 14. The pad 12 is made of a flexible material which can be repeatedly laundered. Such type of materials are well known in the art. The surface 14 also has a generally rectangular area 16 made of upwardly extending fuzzy-like fibers 17. Fibers 17 extend slightly above surface 14.

A piece of tape or elongated section 18 extends across surface 14 and has a surface 20 which contains a plurality of downwardly extending fibers 19. These fibers 19 can selectively engage the surface 14 as well as area 16 of the pad 12. Such type of fibers are well known in the art and are generally referred to as "Velcro". Because such fibers 19 are well known in the art, they will not be discussed in detail herein. The second surface 22 of the tape 18 is a generally smooth.

In the preferred embodiment of the present invention, tape 18 is joined to the pad 12 by stitching 24 disposed at one end of the tape 18. Other methods for joining the tape to the pad 12 are of course within the scope of the present invention.

Located at the other end of the pad 12 from stitching 24 is a grabber member 26. Grabber member 26 is comprised of first and second metal jaws 28 and 30. Grabber 26 is joined to the pad 18 by an outwardly extending, flexible plastic tab member 32. Of course it should be understood that other means for joining grabber 26 to the pad 12 as well as other configuration for grabber 26 are within the scope of the present invention. For example, a plastic gapper member having blunt teeth is also within the scope of this invention. In the preferred embodiment, the grabber 26 is rotatably coupled to the tab 32 by a rivet member 33 or by a like member.

Referring specifically to FIG. 1, one can see that conduits 36 and 38 have been disposed between the tape 18 and the pad 12. Inasmuch as the fibers 19 engages the surface 14 of the pad 12 such conduits 36, 38 are securely held in place. They may be easily removed, however, by merely peeling back the tape 18 as shown in FIG. 2.

In operation of the device 5 of the present invention, the jaws 28 and 30 of gripper 26 would be depressed so as to enable such jaws to engage the bedsheet 9, gown 10 or like material. The jaws are then released and a spring member (not shown) urges them together. However, it should be noted that the jaws 28 and 30 are specifically designed such that while they grab the surface to which they are attached, they do so in a manner which does not puncture such surface. This, as discussed hereinabove, enables the device 5 of the present invention to be joined to such surface without adversely affecting such surface, i.e., there is no puncture formed.

The various conduits 36, 38 to be joined to the pad 12 are then placed on the pad 12 at a desired location. Area 16, formed of fibers 17, forms a somewhat stronger bond with fibers 19 on surface 20 of the tape 18. This enables even small diameter conduits, such as conduit 36, to be joined to pad 12. However, if desired, surface 14 could be made entirely of fibers 17. After the conduits 36, 38 are in position, tape 18 is pressed back against the surface 14 of the pad 12. The conduits 36, 38 are now secured between the tape 18 and pad 12.

While the presently preferred embodiment has been described with respect to a specific configuration, other configurations are of course within the scope of the present invention. For example, pad 12 can have a circular or triangular configuration. Further, a wide range of man-made and natural materials can be used in the construction of the various components of pad 12. In the preferred embodiment, pad 12 has a foam core 40 sandwiched between two pieces of material, all joined together by stitching 42. It is also preferred that all components of the device 5 are chosen such that device 5 can be repeatedly washed. Thus, this invention, is not intended to be limited to the particular embodiments specifically discussed hereinabove.

I claim:

1. A device for holding one or a plurality of medically-related conduits in a secure fashion consisting essentially of a generally flat pad having grip means extending outwardly adjacent one end thereof for selectively joining said pad to a selected fabric-like surface, said grip means comprising first and second jaw members, and a generally flat, flexible strip of material joined to said pad adjacent one end thereof so as to extend across said pad from a position adjacent one end to a position adjacent the other end thereof, said strip of material adapted to be selectively joined to and removed from a surface of said pad thereby securing said conduits thereinbetween.

2. The device according to claim 1 wherein said surface of said pad has an area formed thereon which forms a stronger bond with said strip of material than the remainder of said pad.

3. The device according to claim 1 wherein the length and width of said pad and said strip of material are selected such that at least two conduits can be secured thereinbetween.

4. The device according to claim 1 including in addition thereto, at least one conduit sandwiched between said pad and said strip of material.

5. The device according to claim 1 wherein said jaw members are urged together by a spring.

6. The device according to claim 1 wherein said pad and grip means are made of washable material.

7. The device according to claim 1 wherein said strip of material has a surface which is adapted to be selectively joined to and removed from a surface of said pad thereby securing said conduits thereinbetween.

8. The device according to claim 1 further including a flexible member joined to said pad, and said grip means are rotatably joined to said flexible member.

9. A device for holding one or a plurality of medical conduits in a secure fashion containing:

a generally flat, rectangular pad having an attachment surface and grip means extending outwardly adjacent one end thereof, said grip means having first and second jaws for selectively gripping a bedsheet, hospital gown, bandage or like surface and removably fixing said pad thereto, without puncturing the same; and a generally flat, rectangular flexible strip of material also having an attachment surface for being selectively joined to said attachment surface of said pad, said strip of material joined to said pad adjacent one end thereof such that said strip of material extends across said pad from a position adjacent one end to a position adjacent the other end thereof, whereby said strip of material can be selectively joined to and removed from said pad so as to secure one or more conduits thereinbetween.

10. The device according to claim 9 wherein the length and width of said pad and said strip of material are selected such that at least two conduits can be secured thereinbetween.

11. The device according to claim 9 further including a flexible member joined to said pad, and said grip means are rotatably joined to said flexible member.

* * * * *